US008759443B2

(12) United States Patent
Taden et al.

(10) Patent No.: US 8,759,443 B2
(45) Date of Patent: Jun. 24, 2014

(54) CURABLE BENZOXAZINE-BASED COMPOSITIONS, THEIR PREPARATION AND CURED PRODUCTS THEREOF

(75) Inventors: Andreas Taden, Wittmund (DE); Stefan Kreilling, Duesseldorf (DE); Rainer Schoenfeld, Duesseldorf (DE); Stanley Leroy Lehmann, Martinez, CA (US)

(73) Assignees: Henkel AG & Co. KGaA, Duesseldorf (DE); Henkel IP & Holding GmbH, Duesseldorf (DE)

( * ) Notice: Subject to any disclaimer, the term of this patent is extended or adjusted under 35 U.S.C. 154(b) by 0 days.

(21) Appl. No.: 12/766,112

(22) Filed: Apr. 23, 2010

(65) Prior Publication Data

US 2010/0204385 A1    Aug. 12, 2010

Related U.S. Application Data

(63) Continuation of application No. PCT/US2008/013291, filed on Dec. 2, 2008.

(60) Provisional application No. 60/992,917, filed on Dec. 6, 2007.

(51) Int. Cl.
*C08K 5/35* (2006.01)
*C08G 73/22* (2006.01)

(52) U.S. Cl.
USPC ............................. 524/612; 524/719; 528/424

(58) Field of Classification Search
USPC .................................. 524/612, 719; 528/424
See application file for complete search history.

(56) References Cited

U.S. PATENT DOCUMENTS

| 4,607,091 | A | 8/1986 | Schreiber |
| 5,021,484 | A | 6/1991 | Schreiber et al. |
| 5,200,452 | A | 4/1993 | Schreiber |
| 5,443,911 | A | 8/1995 | Schreiber et al. |
| 5,543,516 | A | 8/1996 | Ishida |
| 6,207,786 | B1 | 3/2001 | Ishida et al. |
| 6,743,852 | B2 | 6/2004 | Dershem et al. |
| 2005/0070634 | A1 | 3/2005 | Lutz et al. |
| 2006/0240261 | A1* | 10/2006 | Helen Li et al. ............ 428/411.1 |

FOREIGN PATENT DOCUMENTS

| JP | 2007-106800 | 4/2007 |
| JP | 2007-146070 | 6/2007 |
| JP | 2007-154018 | 6/2007 |
| WO | 2007064801 | 6/2007 |

OTHER PUBLICATIONS

Takechi, et al., "Synthesis and Thermal Cure of High Molecular Weight Polybenzoxazine Precursors and the Properties of the Thermosets", Polymer, vol. 46, p. 12172-12180, 2006.
Allen, et al., "Physical and Mechanical Properties of Flexible Polybenzoxazine Resins: Effect of Allphatic Diamine Chain Length", Journal of Applied Polymer Science, vol. 101, p. 2798-2809, 2006.
Rimdusit, S. et al., "Toughening of polybenzoxazine by alloying with urethane prepolymer and flexible epoxy: a comparative study", Polym. Eng. Sci., 2005, pp. 288-296, XP001227910.
Yu-Hsin Lee et al., "Effect of rubber reactivity on the morphology of polybenzoxazine blends investigated by atomic force microscopy and dynamic mechanical analysis", Journal of Applied Polymer Science, vol. 100, No. 3, pp. 2443-2454, (2006) XP55022656.
Jang Jyongsik et al., "Performance Improvement of Rubber-Modified Polybenzoxazine", Journal of Applied Polymer Science, John Wiley & Sons, Inc., vol. 67, No. 1, pp. 1-10, (1998) XP002304238.
Dipl-ing Gietl T et al., "The efficiency of various toughening agents in novel phenolic type thermoset resin systems", Journal of Materials Science, Kluwer Academic Publishers, Bo, vol. 41, No. 2, pp. 8226-8243, (2006) XP019450953.
Ghosh et al., "Polybenzoxazines-New high performance thermosetting resins: Synthesis and properties", Progress in Polymer Science, Pergamon Press, Oxford, GB, vol. 32, No. 11, pp. 1344-1391 (2007) XP02287789.
Yanjun Cui et al., "Snythesis and characterization of polyurethane/polybenzoxazine-based interpenetrating polymer networks (IPNs)", Polymer International, vol. 52, No. 8, pp. 1246-1248 (2003) XP55022631.
Tsutomu Takeichi et al., "Synthesis and Characterization of Poly (urethanebenzoxazine) Films as Novel Type of Polyurethane/Phenolic Resin Composites", Journal of Polymer Science: Part A: Polymer Chemistry, vol. 38, pp. 4165-4176 (2000) XP55022632.

* cited by examiner

*Primary Examiner* — Kriellion Sanders
(74) *Attorney, Agent, or Firm* — Steven C. Bauman

(57) ABSTRACT

The invention relates to a curable composition comprising: at least one benzoxazine and at least one toughening additive which can be bound to the at least one benzoxazine in the curing process, characterized in that the toughening additive is distributed in the cured composition in form of discrete domains, and that at least 50% of the discrete domains related to the total amount of discrete domains have a maximum length in any direction of space in the range of 10 nm to 500 nm as determined by transmission electron microscopy (TEM).

9 Claims, No Drawings

CURABLE BENZOXAZINE-BASED COMPOSITIONS, THEIR PREPARATION AND CURED PRODUCTS THEREOF

FIELD OF THE INVENTION

The present invention relates to curable benzoxazine macromonomers, a method of preparing curable benzoxazine macromonomers and cured products obtained from the curable benzoxazine macromonomers. More particularly, the present invention relates to improving mechanical and thermal properties of benzoxazine monomers via use of phase-separating tougheners.

DESCRIPTION OF THE PRIOR ART

Benzoxazine polymers lend themselves to making a wide variety of items such as molding compounds, towpregs, and prepregs by being compounded with reinforcing fibers. Benzoxazine polymers are desirable due to their excellent thermal stability and mechanical properties, minimal side reactions, and reasonably fast curing rates. At the same time, benzoxazine polymers have a relatively straightforward chemistry and can be made from reactants that are more economical than other thermoset polymers, such as bismaleimides, polyimides, and cyanate ester resins ranging in the same desired application temperature range as benzoxazine polymers. In comparison, a basic benzoxazine polymer well known in the art and made from two moles of aniline, one mole of bisphenol A, and four moles of formaldehyde has a very reasonable manufacturing cost.

There are several approaches making use of benzoxazine chemistry. In some approaches monobenzoxazines made from monophenols like phenol, monoamines like aniline and formaldehyde are employed to form polymers. However those compounds have low viscosity and undesirably high vapor pressure and the products obtained after curing show low crosslinking density.

Other approaches make use of so-called difunctional benzoxazines built either by reacting diamines with monophenols or diphenols with monoamines and formaldehyde. The advantage of those compounds over monobenzoxazines is their medium to high viscosity, low vapor pressure and reasonably high crosslinking density after curing.

In yet another approach, diamines and diphenols together with an appropriate amount of formaldehyde have been used to synthesize benzoxazines with more than two benzoxazine moieties per molecule.

In one study Takeichi, Kano & Agag (published in Polymer 46 (2005) pp. 12172-12180) investigated the influence of aliphatic diamines differing in chain length, which were used in the preparation of benzoxazines with bisphenol A and paraformaldehyde, on the elongation of break of the cured benzoxazine film. Compared to aromatic diamines they exhibit lower strength and modulus. However, the biggest of the long-chained aliphatic diamines investigated had a chain length of only six carbon atoms between the two amino groups.

US 2003/0023007 discloses low molecular weight primary aromatic amine end-capped benzoxazines and their use for producing molding compounds, towpregs and prepregs by being compounded with reinforcement fibers. However, the inventors made use of diamines and diphenols having relatively small molecular dimensions and the target product had a very low molecular weight due to extensive end-capping of the product.

In yet another publication of Allen & Ishida (Journal of Applied Polymer Science, 101 (2006) pp. 2798-2809) the effect of aliphatic diamine chain length on physical and mechanical properties of flexible polybenzoxazine resins was investigated. The longest diamine used in the synthesis of monobenzoxazines was 1,12-diamino dodecane.

In three publications of Japanese Patent Applications Nos. 2007-146070, 2007-154018 and 2007-106800 Yuji, Kazuo & Hatsuo presented benzoxazine monomers derived from formaldehyde, diphenols and different diamines. In JP-A 2007-154018 hexamethylene diamines with methyl group substituents on the hexamethylene chain were found to provide thermosetting resins, which excel in dielectric properties and having improved dielectric constant and reduced dielectric loss. The same improvement was found in JP-A 2007-106800 for alternatively employing a diamine containing an aliphatic radical with a benzene ring between the two amino groups. Finally a further alternative to solve the permittivity problem is published in JP-A 2007-146070 wherein as the only diamine in the preparation of the benzoxazines polysiloxane diamines with up to ten Si atoms are disclosed.

However, none of the before-mentioned benzoxazines is able to serve the need for a benzoxazine-based toughening additive to be used in a wide range of monobenzoxazine and/or dibenzoxazine based curable formulations as for example moulding compounds, composite materials, reactive adhesives and sealants and coating materials. In particular, thermosetting products exhibiting high tensile strength, high grass transition temperatures and high elastic modulus (modulus E) without simultaneously exhibiting inferior fracture toughness, notch impact resistance and strain at break are demanded. Therefore increasing fracture toughness, notch impact resistance and strain at break without loss of tensile strength, lowered glass transition temperatures and elastic modulus of such cured materials is one goal of the present invention.

SUMMARY OF THE INVENTION

It was surprisingly found that the above needs can be served by a curable benzoxazine-based composition containing at least one benzoxazine and at least one toughening additive which can be bound to the at least one benzoxazine in the curing process, wherein the toughening additive is distributed in the cured composition in form of discrete domains, and that at least 50% of the discrete domains related to the total amount of discrete domains have a maximum length in any direction of space in the range of 10 nm to 500 nm as determined by transmission electron microscopy (TEM).

Preferably at least 60%, more preferably at least 75% and most preferably at least 90% of the discrete domains related to the total amount of discrete domains have a maximum length in any direction of space in the range of 10 nm to 500 nm as determined by transmission electron microscopy.

Preferably the maximum length of the domains in any direction of space is in the range of about 20 to about 300 nm, most preferably about 25 to about 200 nm as determined by transmission electron microscopy. Preferably at least 60%, more preferably at least 75% and most preferably at least 90% of the discrete domains are falling in any of the before-mentioned preferred discrete domain size ranges.

If the discrete domain size is to be determined in curable compositions containing further particulate material, such as nanosilica particles or the like, a blank preparation having the same composition (apart from the particulate material) is prepared to determine the discrete domain sizes and discrete domain size distribution.

In particular it was surprising to find that the desired improvement regarding the critical energy release rate (G1c) of cured benzoxazine-based resins can be achieved by providing the above described curable compositions.

DETAILED DESCRIPTION OF THE INVENTION

To enable the one skilled in the art to produce such curable compositions of the invention, tougheners, in particular thermoplastic tougheners are suitable to form the phase-separated discrete domains in a benzoxazine matrix. Such thermoplastic tougheners will be described in the following.

Benzoxazine-Based Thermoplastic Tougheners

Benzoxazine-based tougheners are curable tougheners consisting of a curable benzoxazine macromonomer.

Such curable benzoxazine macromonomers contain at least 3 benzoxazine rings and at least one aliphatic, heteroaliphatic, araliphatic, hetereoaraliphatic, aromatic or heteroaromatic fragment, the fragment comprising a shortest atom chain containing at least 40 consecutive atoms between two benzoxazine nitrogen atoms or between two benzoxazine oxygen atoms, and said atom chain must not include any oxazine ring atoms. Preferably said curable benzoxazine macromonomers comprise at least 50, more preferably at least 70 and most preferably at least 100 consecutive atoms between two benzoxazine nitrogen atoms or between two benzoxazine oxygen atoms, and said atom chain must not include any oxazine ring atoms.

The counting of the shortest atom chain between two benzoxazine nitrogen atoms can be exemplified on the following structure:

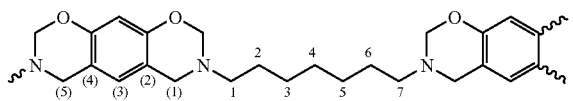

The shortest atom chain contains 7 consecutive atoms. Since the shorter atom chain containing 5 consecutive atoms marked with numbers in brackets includes oxazine ring atoms (atom marked (1)) it is not an allowable atom chain in determining the shortest atom chain.

The counting of the shortest atom chain between two benzoxazine oxygen atoms can be exemplified on the following structure:

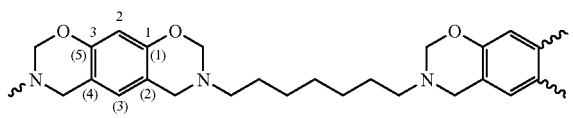

The shortest atom chain contains 3 consecutive atoms. The atom chain containing 5 consecutive atoms marked with numbers in brackets is longer and therefore not the shortest atom chain. An atom chain including any oxazine atoms is again not allowable in determining any atom chain length.

The minimum length of the at least one fragment in the curable benzoxazine macromonomer, which comprises a shortest atom chain containing at least 40 consecutive atoms between two benzoxazine nitrogen atoms or between two benzoxazine oxygen atoms, and which must not include any oxazine ring atoms, ensures the fragment being flexible enough to fulfill the requirement of phase-separation in the benzoxazine resin.

Such benzoxazine macromonomers can be prepared from primary polyamines, preferably diamines and polyphenols, preferably diphenols of different chemical nature in the presence of formaldehyde or a formaldehyde releasing compound, such as paraformaldehyde, trioxane, polyoxymethylene, or formalin.

Whereas the benzoxazine macromonomers exhibit a thermoplastic behavior, the products obtained by curing the benzoxazine macromonomers are thermoset. The curing reaction can be carried out by heating with or without additional catalysts or additives; however at lower temperatures the use of a catalyst is necessary in most cases.

The curable benzoxazine macromonomers may be linear or branched. Linear products are obtained by the use of diamines and diphenols. Incorporation of amines with more than two primary amino groups or polyphenols with more than two phenolic hydroxyl groups leads to branched macromonomers.

The term "benzoxazine macromonomer" as used in the present invention refers to an oligomer or polymer, comprising at least one polymerizable benzoxazine unit.

The term "polymerizable benzoxazine unit" refers to a structural element of an oligomer or polymer, comprising at least one benzoxazine ring, wherein the benzoxazine ring exhibits a ring-closed structure.

Part of the at least 3 benzoxazine rings in the curable benzoxazine macromonomer of the present invention can be "ring-opened" and will still be counted as benzoxazine ring in the meaning of the present invention, i.e. may have a structure

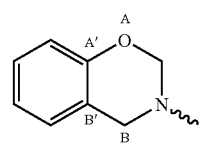

where the covalent bond between atom A and A' or atom B and B' is opened, rather than

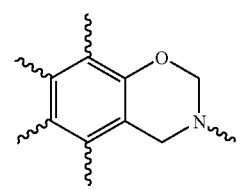

Further examples for ring-opened structures are given below.

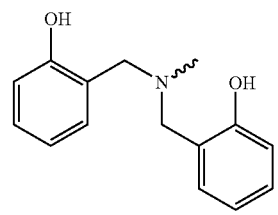

-continued

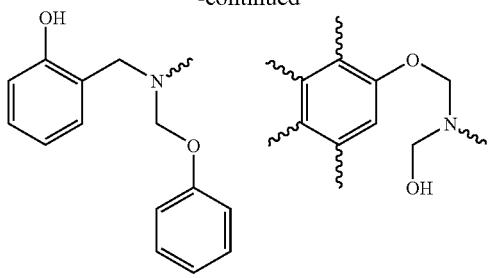

The ring-opened structure influences the properties of the curable benzoxazine macromonomer in that it renders it less rigid and exhibiting improved ductility. The number of ring-opened structures is usually not more than 60%, preferably not more than 40 and most preferably not more than 20% of the total number of ring-closed and ring-opened benzoxazine structures.

Using different combinations of polyamines and/or polyphenols, the properties, such as glass transition temperature, viscosity and solubility of the thermoplastic curable benzoxazine macromonomers can be varied in a wide range. Therefore the benzoxazine macromonomers can be fluid to solid and the glass transition temperature of the cured materials can be varied from about −100° C. to far more than 200° C. Even cured material having more than one glass transition temperature can be obtained. Choosing one or more different, long-chained, so-called "soft" fragments having the above-mentioned at least 40-atom-chains allows the adjustment of miscibility and compatibility to various resins as well as the adjustment of inner phase structures of different resins, when the curable benzoxazine macromonomer is used as toughener to improve impact resistance and to give a high glass transition temperature and elastic modulus simultaneously.

The curable benzoxazine macromonomers excel by their good resistance to solvents and good storage stability at room temperature and even up to 40 to 60° C. They further show a reduced cold flow.

The curable benzoxazine macromonomer tougheners can be prepared in a solvent, the reactants including at least one polyphenol, at least one primary polyamine and formaldehyde or a reactant releasing formaldehyde. The method of preparing those tougheners comprises: combining said reactants, heating the mixture of said reactants under reflux, removing water from the reaction mixture, and separating the curable benzoxazine macromonomer from the solvent, whereby at least one of the polyphenols is such, that the shortest atom chain between two phenolic hydroxyl groups contains at least 40 atoms; and/or at least one of the primary polyamines is such, that the shortest atom chain between two primary amino groups contains at least 40 atoms.

In particular a high content of "soft" fragments of e.g. 50% by weight based on the total weight of the curable benzoxazine macromonomer or even higher, such as 70 or 80% by weight will result in highly preferred tougheners.

The chemical constitution of the soft fragments can vary in very wide ranges and can e.g. be chosen from polyethers, polyesters, polyurethanes, poly(meth)acrylates, polybutadienes and the like, as well as polydialkylsiloxanes or hydrocarbon residues containing siloxanes. Besides polymers, long-chain oligomers and monomers can be used as well. In general the soft fragment is free customizable and can e.g. be built by polyurethane chemistry.

In a further preferred embodiment the toughener includes a mixture of two or more soft fragments within one curable benzoxazine macromonomer to adjust the properties to be compatible with the resin matrix in which the curable benzoxazine macromonomer is to be incorporated to form the discrete domains. The compatibility with the matrix must be good enough to homogeneously dissolve the toughener in the benzoxazine resins and to prevent macroscopic phase separations of the components.

In general the soft fragments are introduced into the curable benzoxazine macromonomer by the choice of primary polyamines and polyphenols.

The term "primary polyamine" describes a compound containing at least two primary amino groups.

The term "polyphenol" describes a special kind of polyol, being an aromatic compound containing at least two phenolic hydroxyl groups in the molecule. A "phenolic hydroxyl group" is considered any hydroxyl group bound to a benzene or naphthaline residue. The at least two phenolic hydroxyl groups can be bound to the same or different benzene or naphthaline residues and at least one of the carbon atoms adjacent to the carbon atom to which the phenolic hydroxyl group is bound has to be bound to hydrogen (—CH=).

The preferred primary polyamines and polyphenols are diamines and diphenols.

In a diamine or a diphenol the soft fragment equals the fragment between the two amino groups and the two phenolic hydroxyl groups, respectively, and the shortest atom chain containing 40 consecutive atoms is the shortest atom chain between the two amino groups and the two phenolic hydroxyl groups, respectively.

An example for the calculation in a triphenol (Trisphenol PA) is given below:

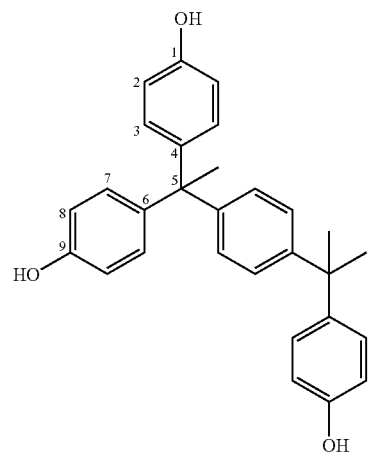 [SMILES: CC(C)(c1ccc(O)cc1)c1ccc(C(C)(c2ccc(O)cc2)c2ccc(O)cc2)cc1]

The meaning of the term "shortest atom chain between two phenolic hydroxyl groups" can easily be demonstrated for the above Trisphenol PA. The shortest atom chain between two phenolic hydroxyl groups is the atom chain, wherein the atom chain is marked with numbers "1" to "9", starting with the carbon atom marked "1" and ending with the carbon atom marked "9". The carbon atom to which the third hydroxyl group is attached is separated from either carbon atom marked "1" or "9" by 14 carbon atoms. Therefore the atom chain between the third hydroxyl group and any one of the other hydroxyl groups contains 14 carbon atoms and is accordingly not the shortest atom chain between two phenolic hydroxyl groups. However Trisphenol PA is not suitable as the "at least one polyphenol, wherein the shortest atom chain between two phenolic hydroxyl groups contains at least 40 atoms", since the shortest carbon atom chain contains only 9 carbon atoms.

Polyphenols meeting the requirement, that the shortest atom chain between two phenolic hydroxyl groups must contain at least 40 atoms can easily be synthesized from long chain compounds sufficiently long, that the shortest atom chain between terminal groups after terminal group modification with a phenolic hydroxyl group compound meets the above requirement. Exemplified for a diphenol as target compound it can for example be started with an α,ω-hydroxyl terminated polyether diol, polyester diol or polybutadiene diol, reacting said polymer with a diisocyanate to obtain an α,ω-isocyanate terminated polymer and reacting said two isocyanate groups each with one of the above mentioned diphenols or an aminophenol. The chain length of the polyether diol, polyester diol or polybutadiene dial should be chosen so, that after the addition of diisocyanate and diphenol or aminophenol at the respective terminal ends, the shortest atom chain between the two phenolic hydroxyl groups contains at least 40 atoms.

Heteroaliphatic diamines satisfying the requirement that the shortest atom chain between two primary amino groups must contain at least 40 atoms are e.g. $NH_2$—[$CH(CH_3)$ $CH_2$—O]$_{33}$—$CH_2$—$CH(CH_3)$—$NH_2$ (Jeffamine® D-2000; Huntsman Corp.) or $H_2N$—$(CH_2)_3$—$Si(CH_3)_2$[O—$Si(CH_3)_2$]$_{34-41}$—$(CH_2)_3$—$NH_2$ (reactive silicon oil, Fluid NH 40 D, Wacker Chemie AG).

Aromatic diamines satisfying the requirement that the shortest atom chain between two primary amino groups must contain at least 40 atoms are e.g. $NH_2$-(p-Ph)—CO—[O—$(CH_2)_4$]$_{9-10}$—O—CO-(p-Ph)—$NH_2$ (p-Ph=para-phenylen; Versalink P 650, Air Products) and $NH_2$-(p-Ph)—CO—[O—$(CH_2)_4$]$_{13-14}$—O—CO-(p-Ph)—$NH_2$ (p-Ph=para-phenylen; Versalink® P 1000, Air Products).

An example for an heteroaliphatic triamine satisfying the requirement that the shortest atom chain between two primary amino groups must contain at least 40 atoms is e.g. a glycerol-started poly(oxypropylene)triamine, wherein the sum of the oxypropylene residues of all three chains is approximately 50 (Jeffamine® T-3000, Huntsman).

The polyphenol or primary polyamine used to introduce the soft fragment into the curable benzoxazine macromonomer preferably has a weight average molecular weight of at least about 600 to about 20,000 g/mol and more preferably at least about 800 to about 5,000 g/mol and even more preferably at least about 900 to about 4,000 g/mol. The weight average molecular weight can be determined by gel permeation chromatography (GPC) using a polystyrene standard.

The glass transition temperatures of the soft fragment or soft fragments of the curable benzoxazine macromonomer are preferably lower than about 100° C., more preferably lower than about 60° C. and most preferably lower than about 25° C. The glass transition temperature can be determined using a differential scanning calorimeter and the transition peak assignment can be carried out by comparative measurements.

The weight average molecular weight of the curable benzoxazine macromonomer of the present invention preferably ranges from about 2,000 g/mol to about 1,000,000 g/mol, more preferably from about 3,000 to about 500,000 g/mol and most preferably from about 5,000 to about 400,000 g/mol. The weight average molecular weight can be determined by gel permeation chromatography (GPC) using a polystyrene standard. In case the molecular weight is higher than 1,000,000 g/mol viscosity is deteriorating processability. In case the molecular weight is below 2,000 g/mol the usability as toughener is decreased.

One big advantage of the tougheners is to provide a "tool box" system to customize curable benzoxazine macromonomers for a large variety of purposes in a large variety of technical fields. The employment of soft fragments having different solubility parameters increases compatibility with many resinous formulations in which the curable benzoxazine macromonomers can be used as reactive additives such as tougheners.

If for example a polyethylene oxide chain is used as a soft fragment, the curable benzoxazine macromonomers of the present invention will be more hydrophilic compared to polydimethyl siloxane chains as a soft segment. However there is a wide range of possibilities to choose from in between the two extremes. One skilled in the art knows that hydrophobicity of polymeric chains is increased in the following order: polyethylene oxide, polypropylene oxide, polytetrahydrofuran, polybutadiene to polydimethyl siloxane. It is further known that a homopolymer of ethylene oxide can be hydrophobized by copolymerization with propylene oxide to obtain a polymeric chain with a solubility parameter between polyethylene oxide and polypropylene oxide.

Moreover hydrophobicity and hydrophilicity, respectively, and therewith compatibility to other resinous formulations, can also be adjusted by not only incorporating one kind of soft fragment into the curable benzoxazine macromonomers, but by incorporating two or more different soft fragments. Since varying the weight fractions of soft fragments is very easy and allows to use soft fragments the monomers of which are not copolymerizable, it is preferred to incorporate two or more different soft fragments into the curable benzoxazine macromonomers of the present invention. The different soft fragments can be incorporated into the curable benzoxazine macromonomers of the present invention by using two or more different soft fragment containing polyamines having primary amino groups, by using two or more different soft fragment containing polyphenols or by using a mixture of at least one soft fragment containing polyamine having primary amino groups with at least one polyphenol containing another soft fragment. Of course the ratio of the soft fragment containing reactants can also be varied to have a maximum degree of freedom in varying different soft fragments.

In the same way soft fragments are defined, it is possible to define "hard" fragments of the curable benzoxazine macromonomers on basis of the atom chain length and molecular weight. The hard fragments (also called "rigid" fragments) contain as shortest atom chain to connect two benzoxazine nitrogen atoms or two benzoxazine oxygen atoms, an atom chain of less than 40 consecutive atoms. However said atom chain must not include any oxazine ring atoms. In general it can be stated that the hard character of hard fragments is more distinct the shorter the atom chain is. Preferably the hard fragment contains as shortest atom chain to connect two benzoxazine nitrogen atoms or two benzoxazine oxygen atoms, an atom chain of less than 25, even more preferable less than 20 and most preferable less than 15 consecutive atoms.

Most preferred rigid polyphenols are rigid diphenols. The most simple of such diphenols are 1,2-dihydroxy benzene, 1,3-dihydroxy benzene and 1,4-dihydroxy benzene, wherein the two phenolic hydroxyl groups are attached to the same benzene residue. A diphenol with two phenolic hydroxyl groups attached to different benzene residues is, e.g. biphenyl-4,4'-diol (also known as "4,4'-Biphenol"). Other suitable examples for diphenols are, e.g. bisphenol A, bisphenol P, bisphenol M, bisphenol F, bisphenol S, bisphenol AP, bisphenol E, 4,4'-oxydiphenol, 4,4'-thiodiphenol, bis(4-hydroxyphenyl)methanone, biphenyl-2,2'-diol, 4,4'-(cyclohexane- 1,1-diyl)diphenol or 4,4'-(3,3,5-trimethylcyclohexane-1,1-diyl)diphenol (bisphenol TMC).

Examples for rigid aliphatic diamines are alkylene diamines like ethane-1,2-diamine, propane-1,3-diamine, propane-1,2-diamine, 2,2-dimethylpropane-1,3-diamine and hexane-1,6-diamine, or aliphatic diamines containing cyclic structures like 4,4'-methylenedicyclohexanamine (DACHM), 4,4'-methylenebis(2-methylcyclohexanamine) (Laromin C260) and 3-(aminomethyl)-3,5,5-trimethylcyclohexanamine (isophorone diamine (IPDA)).

Examples for rigid heteroaliphatic diamines are $H_2N$—$(CH_2)_3$—$N(CH_3)$—$(CH_2)_3$—$NH_2$, $H_2N$—$(CH_2)_3$—$O$—$(CH_2)_4$—$O$—$(H_2)_3$—$NH_2$, $NH_2$—$[CH(CH_3)CH_2$—$O]_{2.5}$—$CH_2$—$CH(CH_3)$—$NH_2$ (Jeffamine® D-230; Huntsman Corp.), $NH_2$—$[CH(CH_3)CH_2$—$O]_6$—$CH_2$—$CH(CH_3)$—$NH_2$ (Jeffamine® D-400; Huntsman Corp.) and $H_2N$—$(CH_2)_3$—$Si(CH_3)_2$—$[O$—$Si(CH_3)_2]_{10-15}$—$(CH_2)_3$—$NH_2$ (reactive silicon oil, Fluid NH 15 D, Wacker Chemie AG).

An example for a rigid araliphatic diamine is m-xylylene diamine (MXDA).

Examples for rigid aromatic diamines are benzene-1,3-diamine, benzene-1,4-diamine, 4,4'-methylenedianiline, 4,4'-oxydianiline, 4,4'-thiodianiline, 4,4'-sulfonyldianiline, 3,3'-sulfonyldianiline, 4,4'-(2,2'-(1,4-phenylene)bis(propane-2,2-diyl))dianiline (Bisaniline P) and $NH_2$-(p-Ph)—CO—[O—$(CH_2)_4]_{3-4}$—O—CO-(p-Ph)—$NH_2$ (p-Ph=paraphenylen; Versalink P 250, Air Products).

The polyamine or polyphenol used to introduce the hard fragment into the curable benzoxazine macromonomer preferably has a molecular weight of less than about 600 g/mol. More preferably the molecular weight is about 46 to about 500 g/mol and even more preferably at least about 60 to about 450 g/mol. The molecular weight can be determined by mass spectrometry. From the above-mentioned examples for rigid diphenols and rigid primary diamines all examples but one fulfill the preferred requirement to have a molecular weight of less than 600 g/mol. The only exception is the reactive silicon oil Fluid NH 15 D having a higher molecular weight. Even though its molecular weight is more in the range of a soft fragment containing diamines and some of its properties may qualify it to be classified as a soft fragment containing diamine it is herein classified as a "rigid" diamine due to its atom chain of about 27 to 39. Consequently this compound is not employed as a single source of a soft fragment in the present invention.

For most purposes it is preferred that the content of soft segments in weight-% based on the total weight of the curable benzoxazine macromonomer is at least about 50% by weight, more preferably at least about 70% by weight and most preferably at least about 80% by weight.

Particularly preferred structures of curable benzoxazine macromonomers are described by the following formal description.

In a preferred embodiment the curable benzoxazine macromonomer toughener contains covalently bound fragments of the following general formula (I)

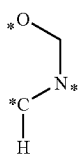

(I)

wherein
the asterisk symbols (*) at the carbon, oxygen and nitrogen atoms depict attachment sites to fragments A and B of the curable benzoxazine macromonomer, fragments A and B being formally attached to the fragment of general formula (I) via single covalent bonds, in that the following formal attachment procedure is carried out:

(a) first at least n fragments of general formula (I) are attached each via their carbon and oxygen attachment sites to adjacent carbon atom attachment sites on one or more benzene or naphthalene residues, which constitute fragment A or which are part of a fragment A to obtain benzoxazine moieties containing n nitrogen attachment sites, whereby n is an integer of two or more; and (b) secondly attaching each of n fragments B having independently m attachment sites, via one of the m attachment sites to one of the nitrogen attachment sites of the fragment obtained in (a), whereby m is an integer of two or more;

(c) thirdly attaching to the n·(m−1) residual attachment sites of the fragment obtained in (b) n·(m−1) fragments independently obtained according to (a) via the nitrogen attachment sites of the fragments obtained according to (a);

(d) subsequently carrying out (b) and (c) repeatedly until the desired length of the resulting benzoxazine macromonomer is reached, whereby the last repetition ends with (b) or (c); and (e) attaching to any remaining attachment site H, OH or $NH_2$.

The one or more of fragments A and B being so constituted, that the shortest chain of atoms between any two attachment sites of said one or more fragments to the oxygen attachment site of the fragment with general formula (I) in case of fragment A and to the nitrogen attachment site of the fragment with general formula (I) in case of fragment B consists of at least 40 atoms.

Particularly preferred fragments A are selected from the group consisting of

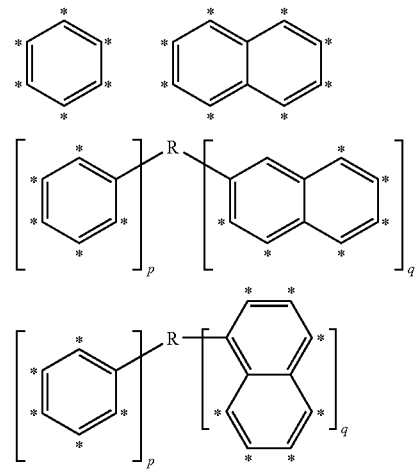

wherein
any two adjacent carbon atoms marked with asterisk symbols (*) may serve as attachment sites to the carbon and oxygen attachment sites of the fragments of general formula (I) and the remaining carbon atoms marked with asterisk symbols (*) are attached to a residue selected from the group consisting of H, a substituted or unsubstituted aliphatic or heteroaliphatic hydrocarbon with 1 to 8 carbon atoms, a substituted or unsubstituted araliphatic or heteroaraliphatic hydrocarbon with 6 to 12 carbon atoms, a substituted or unsubstituted aromatic or heteroaromatic hydrocarbon with 6 to 12 carbon atoms, OH, $NH_2$ or halogen;

the sum of p+q being an integer of two or more;

R being a residue selected from the group consisting of monomeric, oligomeric and polymeric, substituted or unsubstituted, straight-chain or branched, aliphatic, heteroaliphatic, araliphatic, heteroaraliphatic, aromatic or heteroaromatic hydrocarbon residues, siloxane or polysiloxane residues, whereby any of the before-mentioned residues R optionally further contains one or more ester, urethane, urea or ether groups;

and in case p+q=2 the residues R are may also be a single covalent bond directly connecting the thereto attached residues.

Preferred fragments B are selected from the group consisting of monomeric, oligomeric and polymeric, substituted or unsubstituted, straight-chain or branched, aliphatic, heteroaraliphatic, araliphatic, heteroaraliphatic, aromatic or heteroaromatic hydrocarbon residues and siloxane or polysiloxane residues, whereby any of the before-mentioned residues R optionally further contains one or more ester, urethane, urea or ether groups. Most preferred fragments B can be derived from the above described primary polyamines, if the primary amino groups are replaced by "attachment sites".

In one preferred embodiment fragments A are based on one or more benzene fragments only, i.e. they do not contain a naphthaline fragment (q=0). Most preferred are those fragments A wherein p=2 to 6, even more preferable 2 or 3 and q=0, Such structure can be derived from the above described polyphenols, if the phenolic hydroxyl groups are replaced by "attachment sites".

The curable benzoxazine macromonomer toughener of the present invention can be prepared in a solvent, the reactants including at least one polyphenol, at least one primary polyamine and formaldehyde or a reactant releasing formaldehyde, the method of preparing comprising
(i) combining said reactants,
(ii) heating the mixture of said reactants under reflux,
(iii) removing water from the reaction mixture, and
(iv) separating the curable benzoxazine macromonomer from the solvent, whereby
a. at least one of the polyphenols is such, that the shortest atom chain between two phenolic hydroxyl groups contains at least 40 atoms; and/or
b. at least one of the primary polyamines is such, that the shortest atom chain between two primary amino groups contains at least 40 atoms.

In particular, a reaction vessel is kept at a temperature of no warmer than about 250° C., preferably no warmer than about 150° C. and most preferably no warmer than about 10° C. while the reactants are added, preferably under an inert gas atmosphere, such as nitrogen gas. The reaction vessel may be cooled with ice, or any other cooling mechanism. The reactants can be dissolved or dispersed in solvents, such as toluene and/or ethyl acetate, preferably before adding to the vessel. Most preferably the reactants are added in small amount to ensure that the temperature is maintained as desired.

One preferred solvent is a mixture of toluene and ethyl acetate. It is preferred that the ratio of toluene/ethyl acetate be about 8:1 to about 6:1. However, any combination of the aforementioned solvents from about 10:1 to about 4:1 may be employed. Using a combination of solvents is advantageous in that the collection of water by azeotropic distillation is expedited. By contrast, employing either toluene or ethyl acetate alone results in a slow and tedious distillation process.

The combination of solvents is also advantageous in that it allows the separation of water from solvent in a Barrett or Dean-Stark distillation trap to be sharp and allowing nearly all the solvent to be returned to the reaction vessel. However, depending on the solubility of the benzoxazine macromonomer toughener it can also be preferred to use only toluene as a solvent.

Other solvents such as xylene, cyclohexane and chloroform, or water soluble solvents as tetrahydrofuran, dioxane, ethanol or propanol can also be used, however, the water soluble solvents being less preferred, since they are not suitable if the final product is to be separated and purified by washing procedures with aqueous solutions.

In general the reaction mixture is slowly warmed to a temperature at which an exothermic reaction in form of rapid boiling occurs. The vessel is maintained under reflux for about 1 to about 10 hours, preferably 2 to 8 hours and most preferably 4 to 7 hours.

The water byproduct is collected by any method conventional in the art, such as via a Barrett trap. If appropriate, further solvent forming an azeotropic mixture with water, such as toluene or ethyl acetate, may be added during boiling under reflux. Following the above procedure, the yield of the curable benzoxazine macromonomer ranges generally from 90 to 100% of the theoretical yield.

If terminal primary amino groups or terminal phenolic hydroxyl groups should be end-capped, the reaction mixture is cooled down and a compound reactive to primary amino groups or phenolic hydroxyl groups is added, e.g. an isocyanate compound. However terminal primary amino groups can be reacted with monophenols and terminal phenolic hydroxyl groups with monoamins in the presence of formaldehyde or a formaldehyde releasing compound, analogous to the above describe procedure, to yield benzoxazine end-capped benzoxazine macromonomers.

After boiling under reflux the reaction mixture is cooled down and the reaction product is separated from the solvents. The separation can be carried out by washing the reaction mixture, preferably repeatedly, with water and/or 1 N aqueous solution of sodium hydrogen carbonate, separating the organic phase, and optionally washing the organic phase, preferably repeatedly, with a 10% by volume solution of ethanol in water, drying the organic solution over sodium sulfate, removing the sodium sulfate by filtration and evaporating the organic solvent.

To obtain a curable benzoxazine macromonomer toughener having a high molecular weight it is necessary that the stoichiometric ratio of primary amino groups in the polyamine to phenolic hydroxyl groups in the polyphenol is preferably in the range of 0.5 to 2.0, more preferably 0.6 to 1.4, even more preferable 0.8 to 1.2 and most preferable about 1 or about 1.2. Therefore, if only diamines and diphenols are used to prepare the curable benzoxazine macromonomer of the present invention it is preferred to use the diamines and diphenols in an about equimolar ratio.

Another possibility to obtain the curable benzoxazine macromonomer, having a molecular weight as high as described above, is to incorporate an amount of polyamine or polyphenol with more than two primary amino groups and/or more than two phenolic hydroxyl groups, respectively. This will lead to branched and sometimes even partly crosslinked curable benzoxazine macromonomers having high molecular weight. However, if curable benzoxazine macromonomers having good solubility in a wide range of solvents and exhibiting good processability are desired, the sum of the amounts of polyamines with more than two primary amino groups and polyphenols with more than two phenolic hydroxyl groups should be kept low. Preferably the amount of such compounds should not exceed 20% by weight, more preferably 10% by weight, based on the total weight of polyamines with primary amino groups and polyphenols.

To form one benzoxazine ring, one primary amino group, one phenolic hydroxyl group and two formaldehyde molecules are necessary. However it is preferred to use the formaldehyde in excess, the excess preferably being 10% by mol, if a maximum degree of ring-closed structures in the curable benzoxazine macromonomer of the present invention is desired.

Although all the formaldehyde may be provided as formalin, this is an undesirable method because formalin is expensive and it introduces an unnecessary amount of water into the system which must be removed later. However employing formalin in addition to paraformaldehyde in preparing the benzoxazine monomer is advantageous. Paraformaldehyde is preferred as it is significantly less expensive than formalin. Employing formalin in combination with the paraformaldehyde provides enough water and methanol to dissolve the paraformaldehyde. Alternatively, just water may be used. Formalin is also advantageous in that it mitigates the exotherm reaction that occurs at about 80° C. to 85° C. A violent exotherm reaction occurs because as water is generated more paraformaldehyde can dissolve, thus rapidly accelerating the reaction rate. Thus it is advantageous to employ a paraformaldehyde/formalin ratio of at least 1:1, based on the dry weight of the formaldehyde, and preferably of about 8:1 and more. However taking into account the abovementioned drawback of slow reaction, formaldehyde can be employed in water-free form such as paraformalehyde, trioxane or polyoxymethylene only, paraformaldeyde being most preferred.

Other Suitable Thermoplastic Non-Benzoxazine Based Tougheners

Another category of tougheners suitable in the curable compositions of the present invention may be prepared reacting one or more hydroxyl, amino and/or thiol containing polymers, in particular such polymers introducing thermoplastic properties into the prepolymer, with one or more diisocyanates having two isocyanate groups with different reactivity and one or more end-capping agents ("end-cappers") comprising at least one hydroxyl, thiol or amino group being reactive towards isocyanate. Those tougheners are highly preferred in N-arylated benzoxazine based curing systems.

To obtain the tougheners, the hydroxyl, amino and/or thiol containing polymer is reacted with one or more diisocyanates having two isocyanate groups with different reactivity for a time and amount sufficient to ensure isocyanate capping of the hydroxyl, amino and/or thiol containing polymer or oligomer. Thus, the polymer or oligomer may be mixed with one or more diisocyanates having two isocyanate groups with different reactivity and reacted at a temperature in the range of about 50° C. to about 80° C. for a period of about 0.5 to 2.5 hours, desirably under an inert atmosphere, such as a nitrogen blanket, to form an isocyanate-terminated prepolymer intermediate, with which the end-capper is reacted resulting in the formation of the toughener to be used in the compositions of the present invention.

Despite the above described route, alternative routes depending on the nature of the starting reactants can be used to prepare the toughener.

The reaction may also be performed in the presence of a condensation catalyst. Examples of such catalysts include the stannous salts of carboxylic acids, such as stannous octoate, stannous oleate, stannous acetate, and stannous laureate; dialkyltin dicarboxylates, such as dibutyltin dilaureate and dibutyltin diacetate; tertiary amines and tin mercaptides.

When used, the amount of catalyst employed is generally between about 0.00025 and about 5 percent by weight of the catalyzed reactants, depending on the nature of the reactants.

Preferred Thermoplastic Non-Benzoxazine Based Tougheners May be Embraced by the Following Formula (PP-I),

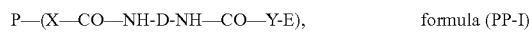

P—(X—CO—NH-D-NH—CO—Y-E)$_z$          formula (PP-I)

where P is a z-valent residue of an oligomer or polymer; X and Y independently are selected from the group consisting of NR', O and S, where R' is hydrogen or a residue selected from the group consisting of aliphatic, heteroaliphatic, araliphatic, heteroaraliphatic, aromatic and heteroaromatic residues; D is a divalent residue of a diisocyanate comprising two isocyanate groups having different reactivity, from which the two isocyanate groups with different reactivity have been removed to form two binding sites (valences); E is an end-capping residue, selected from the group consisting of aliphatic, heteroaliphatic, araliphatic, heteroaraliphatic, aromatic and heteroaromatic residues; and z is an integer of 1 to 12.

Hydroxy, Amino and/or Thiol Containing Polymers P—(XH)$_z$

The polymeric or oligomeric part P of the P—(XH)$_z$ polymer is preferably of such nature to introduce thermoplastic properties to the pre-polymer. Therefore the chemical nature is variable in a wide range embracing polyethers, polyesters, polyamides, polyacrylates, polymethacrylates, polybutadienes, polysiloxanes of which the polyethers are most preferred.

P can be linear or branched. P itself can already include urethane, urea or thiourethane groups originating from the reaction of low-molecular weight polyol, polyamines or polythiols. For example a triol such as glycerol or trimethylolpropane can be reacted with a polyisocyanate such as a diisocyanate to prepare an isocyanate terminated low-molecular weight monomer to which for example polyetherpolyols such as polyether diols can be attached. If such chain-extension reaction is carried out with diisocyanates, it is most preferred to use diisocyanates wherein the two isocyanate groups exhibit different reactivity.

The hydroxyl, amino and/or thiol containing polymer (P—(XH)$_z$, definitions as above) used to make the prepolymer should preferably have a number average molecular weight ("M$_n$") of 500 to 4,000 g/mol more preferably 700 to 2,000 g/mol and most preferably 800 to 1,600 g/mol, as measured by gel permeation chromatography ("GPC") using polyethylene glycol standards for calibration purposes.

The thermoplastic non-benzoxazine based toughener, preferably the non-benzoxazine based toughener of formula (PP-I) thus should have a number average molecular weight in the range of 1,000 to 100,000 g/mol, such as 2,000 to 40,000 g/mol, measured as before with GPC.

The most preferred residue P is a polyalkylene oxide residue. The polyalkylene oxide include a series of hydrocarbon groups separated by oxygen atoms and terminated with hydroxyl, amino or thiol.

The hydrocarbon groups should preferably be alkylene groups—straight or branched chain—and should preferably have from 2 to about 6 carbons, such as about 2 to about 4 carbon atoms, desirably about 3 to about 4 carbon atoms.

The alkylene groups may be thus derived from ethylene oxide, propylene oxides, butylene oxides or tetrahydrofuran. The hydroxyl, amino and/or thiol terminated polyalkylene oxide should preferably have a number average molecular weight of about 500 to about 4,000 g/mol, such as about 700 to about 2,000 g/mol and most preferably 800 to 1,800 g/mol.

For the purpose of the present invention, not only one polymer P—(XH), but also mixtures of polymers P—(XH)$_z$ can be used for the preparation of the thermoplastic non-benzoxazine based toughener, preferably for the preparation of the thermoplastic non-benzoxazine toughener of formula (PP-I). Within those mixtures the chemical nature of P as well as the molecular weights may vary within the described ranges.

A preferred hydroxy-containing polymer to be used as P—(XH)$_z$ can be described by structure XX:

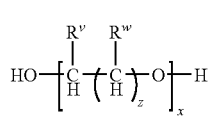

XX where $R^v$ and $R^w$ independently are H, methyl or ethyl, z is 1-6, preferably 2-3 and x is 12-45, such as 20-35. Most preferably in hydroxy-containing compounds of general formula XX one or both of $R^v$ and $R^w$ are H and z is 2 to 3 and the number-average molecular weight determined by the value of x is between 500 and 4000 g/mol more preferably 700 to 2000 g/mol and most preferably 800 to 1600 g/mol.

A preferred amino-containing polymer to be used as P—(XH)$_z$ can be described by structure XXI:

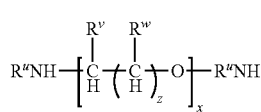

XXI where $R^v$, $R^w$, z and x are defined as in structure XXIII, and $R^u$ is H or alkyl. Those compounds lead to polyurea containing prepolymers.

While structures for the hydroxy and amino containing polymers or oligomers have been shown, alternatives for use herein include the thiol versions thereof. And of course combinations of such compounds may be used herein.

The hydroxy, amino and/or thiol containing polyalkylene ethers should be used in a molar ratio of OH, amino and/or SH groups to isocyanate groups of the one or more diisocyanates having two isocyanate groups with different reactivity in a range of 1:0.9 to 1:4.0, such as 1:1.0 to 1:2.5, for instance 1:1.85.

The integer z in P—(XH)$_z$ ranges from 1 to 12, preferable 1 to 6, more preferable 2 to 4 and most preferable z is 2 or 3.
Diisocyanates Having Two Isocyanate Groups with Different Reactivity D-(NCO), Crucial for the present invention is to use a diisocyanate for reaction with the hydroxy, amino and/or thiol containing polymers P—(XH)$_z$, which has two isocyanate groups having different reactivity. The different reactivity is influenced especially by the spatial requirements, steric hindrances and/or electron density in the vicinity of an isocyanate group at given reaction conditions.

However, in any case of doubt, the difference in reactivity towards P—(XH)$_z$ can be determined easily by the one skilled art under the general reaction conditions used to react the diisocyanate with P—(XH)$_z$. For example 900 MHz $^{13}$C-NMR analysis can clearly distinguish between isocyanate carbon atoms of different reactivity. A $^{13}$C-NMR spectrum taken from the diisocyanate candidate and compared with the reaction product between P—(XH)$_z$ and die diisocyanate candidate will easily reveal a preference of the more reactive isocyanate group of the diisocyanate towards the XH groups of P—(XH)$_z$, in that the NMR signal for the carbon atom of the more reactive isocyanate group will disappear more than the carbon atom signal of the lower reactive isocyanate group. Since the NMR signal intensity is quantifiable the ratio of both reaction products—the one between P-(XH)$_z$ and the more reactive isocyanate group and the one with the less reactive isocyanate group of the diisocyanate—can be determined. Preferably at least 70% by weight of the product should be attributed to the reaction with the more reactive isocyanate group of the diisocyanate. Even more preferably at least 80% by weight and most preferably at least 90% by weight of the reaction product between P—(XH)$_z$ and the diisocyanate having two isocyanate groups with different reactivity should be attributable to the reaction with the more reactive isocyanate group.

Another approach to determine different reactivities of isocyanate groups in a diisocyanate is to react 1 mol of diisocyanate with 1 mol of n-hexanol and to determine the ratio of the products, i.e. monourethane, diurethane and unreacted diisocyanate.

However one skilled in the art can easily use any other textbook approaches to determine different reactivities.

Asymmetric diisocyanates for the purposes of this invention are aromatic, aliphatic or cycloaliphatic diisocyanates, preferably having a molecular weight of about 160 g/mol to 500 g/mol which possess NCO groups having a different reactivity.

Examples of suitable aromatic asymmetric diisocyanates are 2,4-toluene diisocyanate (2,4-TDI), naphthalene 1,8-diisocyanate (1,8-NDI) and 2,4'-methylenediphenyl diisocyanate (2,4'-MDI). Examples of suitable cycloaliphatic asymmetric diisocyanates are 1-isocyanatomethyl-3-isocyanato-1, 5,5-trimethylcyclohexane (isophorone diisocyanate, IPDI), 2-isocyanatopropylcyclohexyl isocyanate, 1-methyl-2,4-diisocyanatocyclohexane or hydrogenation products of the aforementioned aromatic diisocyanates, especially hydrogenated 2,4'-MDI or 4-methylcyclohexane-1,3-diisocyanate (H-TDI). Examples of aliphatic asymmetric diisocyanates are 1,6-diisocyanato-2,2,4-trimethylhexane, 1,6-diisocyanato-2,4,4-trimethylhexane, 2-butyl-2-ethylpentamethylene diisocyanate and lysine diisocyanate. Preferred asymmetric diisocyanates are 2,4-toluene diisocyanate (2,4-TDI) and 2,4'-methylenediphenyl diisocyanate (2,4'-MDI).

In the context of the invention 2,4'-methylenediphenyl diisocyanate (2,4'-MDI) comprehends a polyisocyanate having a 2,4'-MDI content of more than 95% by weight, more preferably of more than 97.5% by weight. Additionally the 2,2'-MDI content is below 0.5% by weight, more preferably below 0.25% by weight.

In the context of the invention 2,4-toluene diisocyanate (2,4-TDI) comprehends a polyisocyanate having a 2,4-TDI content of more than 95% by weight, preferably of more than 97.5% by weight, and very preferably of more than 99% by weight.

End-Capping Agents E-YH

The one or more end-capping used to react with the isocyanate-terminated group of the isocyanate-terminated prepolymer have the general formula E-YH, wherein E is an end-capping residue, selected from the group consisting of aliphatic, heteroaliphatic, araliphatic, heteroaliphatic, aromatic and heteroaromatic residues and YH is selected from NHR', OH and SH with R' being defined as above for the XH group(s) of P—(XH)$_z$.

E can be further substituted for example by reactive functional groups such as OH, primary and secondary amino, thiol, oxazoline, benzoxazine or silane groups. Preferably E is a phenolic group. More preferable E-YH is a bisphenol such as bisphenol A, bisphenol P, bisphenol M, bisphenol F, bisphenol S, bisphenol AP, bisphenol E or bisphenol TMC, or a hydroxyphenyl ether such as p-hydroxyphenyl ether and p-hydroxyphenyl thioether, or 4,4'-dihydroxy benzophenone, 4,4'-Dihydroxydiphenyl, 2,2'-dihydroxydiphenyl, or 4,4'-cyclohexyliden diphenol, resorcinol or hydrochinon.

However E does not necessarily has to contain a reactive functional group or an aromatic residue. For example n-butyl amine can be employed as an end-capper (E=n-butyl and YH=$NH_2$) or cardanol (E=m-$C_{15}H_{31-2n}$-phenyl, with n=0, 1, 2, 3 and YH=OH).

Best results in view of flexural modulus combined with high G1c values are however observed when E is a phenol group and most preferred E-YH is bisphenol A.

The end-capping agent and the isocyanate-terminated prepolymer may be reacted at an appropriate temperature for a sufficient time to cause reaction between the isocyanate groups and the YH groups on the capping agent. Preferably, this reaction continues for a period of about 30 minutes to 4 hours, at a temperature in the range of about 60 to about 100° C., preferably about 70 to about 90° C., most preferably about 80 to about 90° C. A catalyst, such as any of the condensation catalysts discussed above (e.g. dibutyltin dilaurate), may be used to enhance reaction times in preparing the thermoplastic non-benzoxazine based toughener, preferably the thermoplastic non-benzoxazine based toughener of formula (PP-I). Of course combinations of such compounds may be used herein.

As preferably essentially all of the one or more diisocyanates having two isocyanate groups with different reactivity are reacted with the end-capping agent, an appropriate amount of end-capper is to be used to facilitate such reaction. The precise amount of course will depend on the nature, identity and amount of the remaining reactants that are used to form the adduct and as such will be left to the discretion of those persons of ordinary skill in the art.

Benzoxazine Component—Matrix Resin

The matrix resins components to incorporate the above-described tougheners are preferably selected amongst the benzoxazines, the most important of them being described in the following.

The benzoxazine component can be any curable monomer, oligomer or polymer comprising at least one benzoxazine moiety. Preferably monomers containing up to four benzoxazine moieties are employed as the benzoxazine component in form of single compounds or mixtures of two or more different benzoxazines.

In the following a broad spectrum of different suitable benzoxazines containing one to four benzoxazine moieties are presented.

One possible benzoxazine may be embraced by the following structure I:

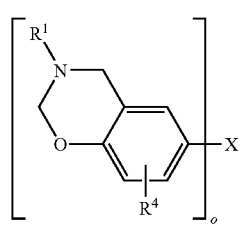

where o is 1-4, X is selected from a direct bond (when o is 2), alkyl (when o is 1), alkylene (when o is 2-4), carbonyl (when o is 2), oxygen (when o is 2), thiol (when o is 1), sulfur (when o is 2), sulfoxide (when o is 2), and sulfone (when o is 2), $R^1$ is selected from hydrogen, alkyl, alkenyl and aryl, and $R^4$ is selected from hydrogen, halogen, alkyl and alkenyl, or $R^4$ is a divalent residue creating a naphthoxazine residue out of the benzoxazine structure.

More specifically, within structure I the benzoxazine may be embraced by the following structure II:

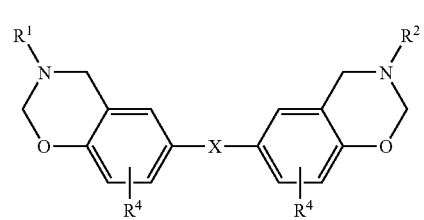

where X is selected from a direct bond, $CH_2$, O, $C(CH_3)_2$, C=O, S, S=O and O=S=O, $R^1$ and $R^2$ are the same or different and are selected from hydrogen, alkyl, such as methyl, ethyl, propyls and butyls, alkenyl, such as allyl, and aryl, and $R^4$ are the same or different and defined as above.

Representative benzoxazines within structure II include:

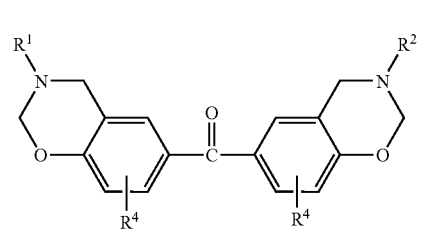

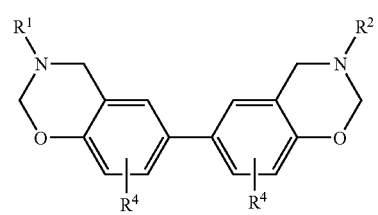

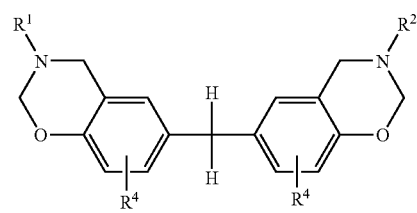

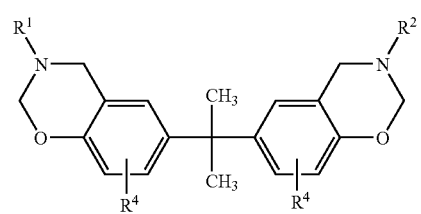

where $R^1$, $R^2$ and $R^4$ are as defined above.

Alternatively, the benzoxazine may be embraced by the following structure VII:

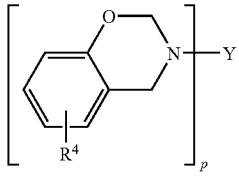

where p is 2, Y is selected from biphenyl (when p is 2), diphenyl methane (when p is 2), diphenyl isopropane (when p is 2), diphenyl sulfide (when p is 2), diphenyl sulfoxide (when p is 2), diphenyl sulfone (when p is 2), and diphenyl ketone (when p is 2), and $R^4$ is selected from hydrogen, halogen, alkyl and alkenyl, or $R^4$ is a divalent residue creating a naphthoxazine residue out of the benzoxazine structure.

Though not embraced by structures I or VII additional benzoxazines are within the following structures:

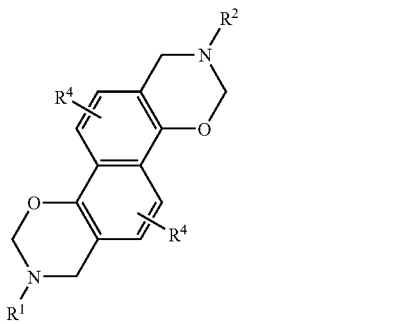

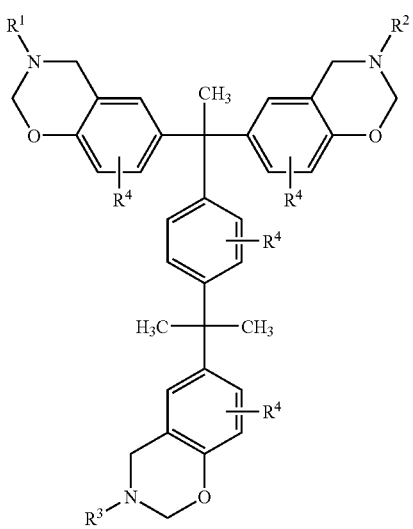

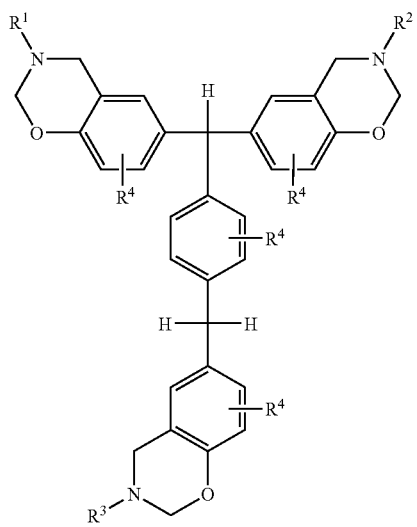

where $R^1$, $R^2$ and $R^4$ are as defined above, and $R^3$ is defined as $R^1$, $R^2$ or $R^4$.

Specific examples of the above generically described benzoxazines include:

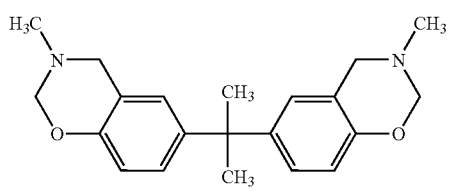

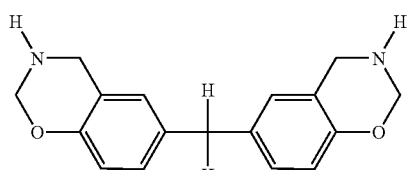

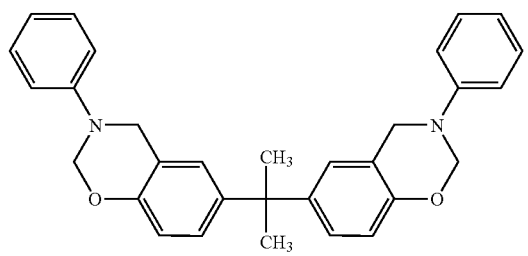

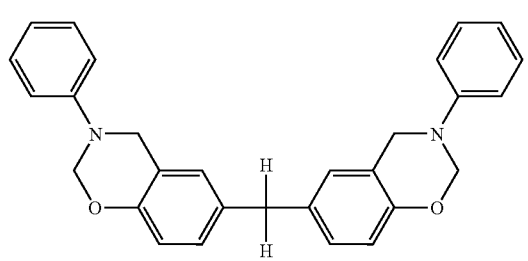

-continued

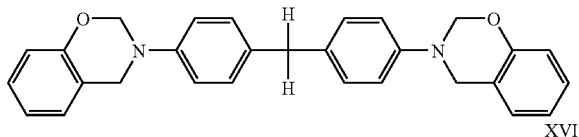

XV

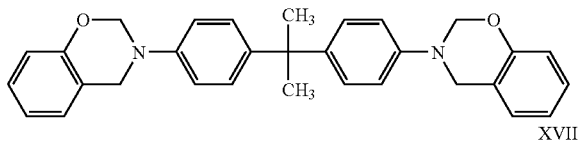

XVI

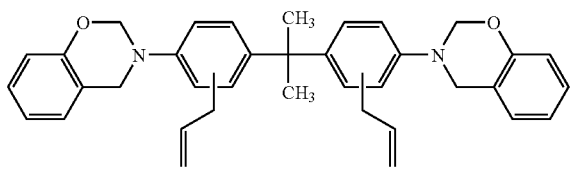

XVII

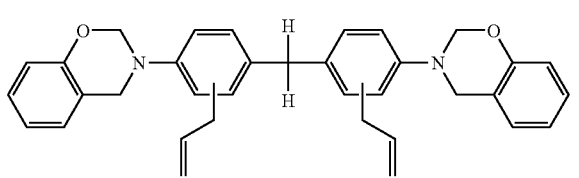

XVIII

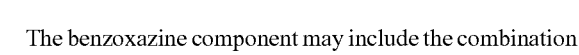

The benzoxazine component may include the combination of multifunctional benzoxazines and monofunctional benzoxazines, or may be the combination of one or more multifunctional benzoxazines or one or more monofunctional benzoxazines.

Examples of monofunctional benzoxazines may be embraced by the following structure XIX:

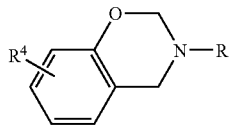

XIX where R is alkyl, such as methyl, ethyl, propyls and butyls, or aryl with or without substitution on one, some or all of the available substitutable sites, and $R^4$ is selected from hydrogen, halogen, alkyl and alkenyl, or $R^4$ is a divalent residue creating a maphthoxazine residue out of the benzoxazine structure.

For instance, monofunctional benzoxazines may be embraced by general structure XX:

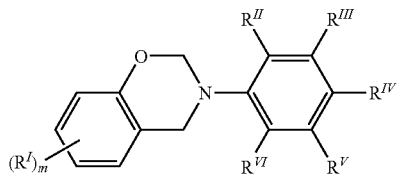

XX where in this case $R^I$ is selected from alkyl, alkenyl, each of which being optionally substituted or interrupted by one or more O, N, S, C=O, COO, and NHC=O, and aryl; m is 0 to 4; and $R^{II}$, $R^{III}$, $R^{IV}$, $R^V$ and $R^{VI}$ are independently selected from hydrogen, alkyl, alkenyl, each of which being optionally substituted or interrupted by one or more O, N, S, C=O, COOH, and NHC=O, and aryl.

Specific examples of such a monofunctional benzoxazine are:

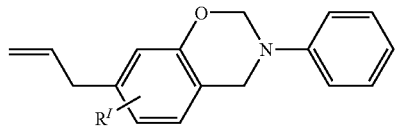

XXI where $R^I$ is as defined above; or

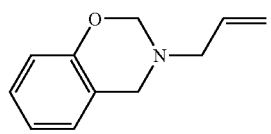

XXII

Benzoxazines are presently available commercially from several sources, including Huntsman Advanced Materials; Georgia-Pacific Resins, Inc.; and Shikoku Chemicals Corporation, Chiba, Japan.

If desired, however, instead of using commercially available sources, the benzoxazine may typically be prepared by reacting a phenolic compound, such as a bisphenol A, bisphenol F, bisphenol S or thiodiphenol, with an aldehyde and an alkyl or aryl amine. U.S. Pat. No. 5,543,516, hereby expressly incorporated herein by reference, describes a method of forming benzoxazines, where the reaction time can vary from a few minutes to a few hours, depending on reactant concentration, reactivity and temperature. See e.g. generally U.S. Pat. No. 4,607,091 (Schreiber), U.S. Pat, No. 5,021,484 (Schreiber), U.S. Pat. No. 5,200,452 (Schreiber) and U.S. Pat. No. 5,443,911 (Schreiber).

Any of the before-mentioned benzoxazines may contain partially ring-opened benzoxazine structures. However, for the purpose of this invention those structures are still considered to be benzoxazine moieties, in particular ring-opened benzoxazine moieties.

The benzoxazine component is preferably the only curable ingredient in the curable compositions of the present invention. However other curable ingredients or resins can be included, if desired.

Curable Compositions

The curable compositions of the present invention can be prepared by any of the above described tougheners and a benzoxazine component as matrix resin component.

Whereas the above described benzoxazine macromonomer tougheners can be used in either N-arylated benzoxazine resins or N-aliphatic benzoxazines or mixtures of both, the other tougheners based on polymers including a diisocyanate residue obtained from a diisocyanate with two isocyanate groups of different reactivity, are most suitable in benzoxazine resin compositions based on N-arylated benzoxazines. However, their use is not limited to N-arylated benzoxazine containing systems.

In general the toughener content based on the total weight of the curable composition of the present invention is in the range of about 1 to 50% by weight, more preferably, 3 to 40% by weight, even more preferable 5 to 30% by weight. However, best results are often obtained in the range of 10 to 25% by weight of toughener content based on the total weight of the curable composition of the present invention.

The main component of the rest of the curable composition is the matrix resin, which can even be the only further component.

For evaluation purposes, i.e. determination of the discrete domain size of the tougheners in the cured composition, no other particulate substances such as fillers, in particulate nanoparticle fillers or pigments and the like must be added.

However further curable ingredients other than the above describes can be added. Examples are epoxy resins, phenol resins, maleinimide resins, oxazolines, isocyanates and the like. Other additives which the inventive compositions can include plasticizers, extenders, microspheres, nanosilica particles, fillers and reinforcing agents, for example coal tar, bitumen, textile fibres, glass fibres, asbestos fibres, boron fibres, carbon fibres, mineral silicates, mica, powdered quartz, hydrated aluminum oxide, bentonite, wollastonite, kaolin, silica, aerogel or metal powders, for example aluminium powder or iron powder, and also pigments and dyes, such as carbon black, oxide colors and titanium dioxide, fire-retarding agents, thixotropic agents, flow control agents, such as silicones, waxes and stearates, which can, in part, also be used as mold release agents, adhesion promoters, antioxidants and light stabilizers, the particle size and distribution of many of which may be controlled to vary the physical properties and performance of the inventive compositions.

Curing of the curable formulations of the present invention to the cured products of the present invention can be self-initiated under elevated temperature conditions and also by inclusion of cationic initiators, such as Lewis acids, and other known cationic initiators, such as metal halides; organometallic derivatives; metallophorphyrin compounds such as aluminum phthalocyanine chloride; methyl tosylate, methyl triflate, and triflic acid; and oxyhalides. Likewise, basic materials, such as imidiazoles, may be used to initiate polymerization. A typical curing temperature without catalyst will be in the range of 150 to 250° C., more preferably in the range of 160 to 220° C. In catalyst containing formulations the curing temperatures can be lowered depending on the catalyst chosen.

In the following the invention will be described in more detail with reference to examples.

EXAMPLES

Example 1

Synthesis of the PU Toughening Additives 1.1 Synthesis of the Pre-Polymer #1 (PU I) using PTHF 1400

101.7 g of polytetrahydrofuran ($M_n$=1400 g/mol) and 1.0 g of trimethylolpropane are mixed and melted at 70° C., and water is removed. To this mixture, 27.1 g of 2,4-toluene diisocyanate are added while stirring. The mixture is then stirred for 40 minutes at 75° C. In a second step, to complete the reaction of the excess isocyanate groups, 33.2 g of bisphenol A and about 30 mg of DBTL are added at 75° C., and the mixture is stirred for 2 hours at 85° C.-90° C. The progress of the reaction is monitored by determining the NCO content of the mixture. The final product does not contain any remaining free NCO groups.

1.2 Synthesis of the Pre-Polymer #2 (PU II) using PTHF 1400/2000 (1:1)

101.7 g of polytetrahydrofuran ($M_n$=1400 g/mol), 144.0 g of polytetrahydrofuran ($M_n$=2000 g/mol), and 2.0 g of trimethylolpropane are mixed and melted at 70° C., and water is removed. To this mixture, 54.2 g of 2,4-toluene diisocyanate are added while stirring. The mixture is then stirred for 40 minutes at 75° C. In a second step, to complete the reaction of the excess isocyanate groups, 66.4 g of bisphenol A and about 30 mg of DBTL are added at 75° C., and the mixture is stirred for 2 hours at 85° C.-90° C. The progress of the reaction is monitored by determining the NCO content of the mixture. The final product does not contain any remaining free NCO groups.

1.3 Synthesis of the Pre-Polymer #3 (PU III) using PTHF 1000/2000 (2:3)

29.0 g of polytetrahydrofuran ($M_n$=1000 g/mol), 87.2 g of polytetrahydrofuran ($M_n$=2000 g/mol), and 1.0 g of trimethylolpropane are mixed and melted at 70° C., and water is removed. To this mixture, 27.1 g of 2,4-toluene diisocyanate are added while stirring. The mixture is then stirred for 40 minutes at 75° C. In a second step, to complete the reaction of the excess isocyanate groups, 33.2 g of bisphenol A and about 30 mg of DBTL are added at 75° C., and the mixture is stirred for 2 hours at 85° C.-90° C. The progress of the reaction is monitored by determining the NCO content of the mixture. The final product does not contain any remaining free NCO groups.

1.4 Synthesis of TBox #1 (TBox I)

Versalink P-1000 (100%), resulting in about 84% to 86%% soft fragments content

In a 2 L three-necked round bottom flask equipped with stirrer, condenser, electric thermometer, dropping funnel and nitrogen gas inlet a cloggy mixture of 20.81 g (0.693 mol; 0.693 eq) paraformaldehyde and 8.03 g (0.099 mol; 0.099 eq) formaldehyde solution (37% in water) in 100 ml toluene was cooled with ice. Under a nitrogen gas atmosphere 232.56 g (0.180 mol; 0.360 eq) Versalink P-1000 solution in 200 ml toluene was added dropwise within 20 minutes at 3.4-7.3° C., resulting in a hazy solution. A solution of 41.09 g (0.180 mol; 0.360 eq) bisphenol A in 100 ml ethyl acetate was added within 5 minutes at 7.0-8.4° C. The hazy reaction mixture was subsequently heated and maintained under reflux conditions for 6 hours while stirring. After the initial heating had been completed, 3×100 ml of toluene were added to the mixture.

While the reaction was progressing, the accumulating water was removed by distillation using a water separator. The volume of water obtained was 7.1 ml after 1 hour, 13 ml after 3 hours, and 13 ml after 6 hours, corresponding to 75% of the theoretically formed volume of 17.2 ml of water.

The clear solution resulting from the above reaction was washed three times with a solution of $NaHCO_3$ (1N) and three times with 10% ethanol in water. All phase separations took place very slowly. The organic phase was then dried over sodium sulfate and concentrated using a rotary evaporator. Remaining solvents were removed in a vacuum drying cabinet.

282 g of product were obtained, corresponding to 100% of the theoretical yield (282.3 g).

1.5 Synthesis of TBox #2 (TBox II)

Versalink P-1000 and Jeffamin D2000 (87.5: 12.5), resulting in about 81% to 85% soft fragments content In a 2 L three-necked round bottom flask equipped with stirrer, condenser, electric thermometer, dropping funnel and nitrogen gas inlet a cloggy mixture of 17.95 g (0.5679 mol; 0.5679 eq) paraformaldehyde and 6.58 g (0.0811 mol; 0.0811 eq) formaldehyde solution (37% in water) in 120 ml toluene was cooled with ice. Under nitrogen gas atmosphere 175.00 g (0.1354 mol; 0.2708 eq) Versalink P-1000 solution in 270 ml toluene was added dropwise within 20 minutes at 3.4-6.6° C., resulting in a milky, hazy solution. A solution of 25.00 g (0.0121 mol; 0.0242 eq) Jeffamin D2000 in 70 ml toluene was added dropwise within 7 minutes at 5.3-6.0° C. A solution of 33.67 g (0.1475 mol; 0.2950 eq) bisphenol A in 100 ml ethyl acetate was added within 5 minutes at 5.5-8.2° C. The milky, hazy reaction mixture was then heated and maintained under reflux conditions. After 1 hour, the mixture was getting viscous, and 200 ml of toluene were added. While the reaction was progressing, the accumulating water was removed using a water separator. The volume of water obtained was 8.5 ml after 1 hour, 10 ml after 2 hours, 10.2 ml after 3 hours, and 10.2 ml after 6 hours, corresponding to 72% of the theoretically formed volume of 14.1 ml of water. The reaction was terminated after 6 hours. While cooling down, the product was diluted again with toluene.

The solution resulting from above reaction was washed three times with a solution of $NaHCO_3$ (1N) and three times with 10% ethanol in water. The organic phase was then dried over sodium sulfate, and concentrated using a rotary evaporator. Remaining solvents were removed in a vacuum drying cabinet at 50° C.

220 g of product (yellow, viscous) were obtained, corresponding to 91% of the theoretical yield (240/g).

1.6 Synthesis of TBox #3 (TBox III)

Versalink P-1000 and Jeffamin 02000 (50:50), resulting in about 83% to 87% soft fragment content In a 2 L three-necked round bottom flask equipped with stirrer, condenser, electric thermometer, dropping funnel and nitrogen gas inlet a cloggy mixture of 16.87 g (0.5336 mol; 0.5336 eq) paraformaldehyde (95%) and 6.18 g (0.0762 mol; 0.0762 eq) formaldehyde solution (37% in water) in 100 ml toluene was cooled with ice. Under nitrogen gas atmosphere a solution of 110.00 g (0.0535 mol; 0.1070 eq) Jeffamin D2000 in 130 ml toluene was added dropwise within 15 minutes at 4.7-9.8° C., resulting in a milky, hazy solution. A solution of 110.00 g (0.0851 mol; 0.1702 eq) Versalink P-1000 in 250 ml toluene was added dropwise within 15 minutes at 3.2-5.4° C. A solution of 31.64 g (0.1386 mol; 0.2772 eq) bisphenol A in 120 ml ethyl acetate was added within 5 minutes at 4.5-6.0° C. The milky, hazy reaction mixture was then heated and maintained under reflux conditions, while the mixture was slowly getting clear. While the reaction was progressing, the accumulating water was removed using a water separator. The volume of water obtained was 5.5 ml after 2 hours, and 6.5 ml after 6 hours, corresponding to 49% of the theoretically formed volume of 13.2 ml of water. The reaction was terminated after 6 hours.

The clear solution resulting from above reaction was washed three times with a warm solution of $NaHCO_3$/NaCl (containing 4 parts 1N $NaHCO_3$ in water and 1 part saturated NaCl solution in water), and three times with a ethanol/NaCl solution (containing 4 parts aqueous ethanol (10% ethanol) and 1 part saturated NaCl solution in water). The phase separations took place slowly. The organic phase was then dried over sodium sulfate, and concentrated using a rotary evaporator. Remaining solvents were removed in a vacuum drying cabinet at 50° C.

242.4 g of product (yellow, viscous) were obtained, corresponding to 93.8% of the theoretical yield (258.3 g).

1.7 Synthesis of TBox #4 (TBox IV)

Jeffamin 02000 (100%), resulting in about 85% to 89% soft fragment content

In a 2 L three-necked round bottom flask equipped with stirrer, condenser, electric thermometer, dropping funnel and nitrogen gas inlet a cloggy mixture of 22.95 g (0.726 mol) paraformaldehyde (95%) and 100 ml toluene was cooled with ice. Under nitrogen gas atmosphere a solution of 339.24 g (0.165 mol; 1 eq) Jeffamin 02000 in 300 ml toluene was added dropwise and slowly at max. 10° C. A solution of 37.66 g (0.165 mol) bisphenol A in 120 ml ethyl acetate was added likewise. The milky, hazy reaction mixture was then heated and maintained under reflux conditions, while the mixture was slowly getting clear. While the reaction was progressing, the accumulating water was removed using a water separator. The reaction was terminated after 6 hours.

The clear solution resulting from above reaction was washed three times with a warm solution of $NaHCO_3$/NaCl (containing 4 parts 1N $NaHCO_3$ in water and 1 part saturated NaCl solution in water), and three times with a ethanol/NaCl solution (containing 4 parts aqueous ethanol (10% ethanol) and 1 part saturated NaCl solution in water). The phase separations took place slowly. The organic phase was then dried over sodium sulfate, and concentrated using a rotary evaporator. Remaining solvents were removed in a vacuum drying cabinet at 50° C.

381.44 g of product (yellow, viscous) were obtained, corresponding to 96.15% of the theoretical yield (384.84 g).

1.8 Synthesis of TBox #5 (TBox V)

Jeffamin D2000 and a bisphenol A-functionalized PU prepolymer (70:30), resulting in about 92% to 96% soft fragment content The synthesis was performed in two steps.

Step 1: Synthesis of Bisphenol A-Functionalized PU Prepolymer

In the first step, a PU prepolymer was synthesized from polybutadiene (Krasol LBH 2000) and TDI (toluene diisocyanate). The end groups were functionalized with bisphenol A for the subsequent use of the bisphenol A-functionalized PU prepolymer as a soft fragment of TBox #5.

210 g (0.1 mol) of polybutadiene diol (Krasol LBH 2000; M=2100 g/mol) was desiccated for 30 minutes at 90° C. using a vacuum oil pump. Under a nitrogen gas atmosphere, 34.8 g (0.2 mol) toluene diisocyanate (TDI) was added at 73° C. The mixture was stirred for 30 minutes at 75° C. under a nitrogen gas atmosphere. To complete the reaction of the excess isocyanate groups, 45.8 g (0.2 mol) of bisphenol A and about 30 mg dibutyltin dilaurate (DBTL) were added at 75° C., and the mixture was stirred for 1.5 hours at 90° C. Then, 50 g of ethyl acetate were added, and the mixture was again stirred for 1.5 hours at 90° C. The progress of the reaction was monitored by determining the NCO content. The final product does not contain any free OH groups.

In order to prepare Step 2, the hydroxyl number of the product was determined (OH number=39) to obtain the molecular weight (2776 g/mol). The product was diluted with toluene to yield a 55% (w/w) solution.

Step 2: Synthesis of TBox #5

In a 2 L three-necked round bottom flask equipped with stirrer, condenser, electric thermometer, dropping funnel and nitrogen gas inlet 16.58 g (0.5245 mol; 0.5245 eq) paraformaldehyde (95%) in 100 ml toluene was cooled with ice. Under nitrogen gas atmosphere, a solution of 245.00 g (0.1192 mol; 0.2384 eq) Jeffamin D2000 in 150 ml toluene was added dropwise within 7 minutes at 2.8-7.1° C., resulting in a hazy solution. A solution of 190.90 g (0.0378 mol; 0.0756 eq) bisphenol A-functionalized PU prepolymer (55% w/w in toluene) in 50 ml toluene was added dropwise within 10 minutes at 3.6-6.3° C. A solution of 18.58 g (0.0814 mol;

0.1628 eq) bisphenol A in 100 ml ethyl acetate was added within 3 minutes at 5.8-7.9° C. The milky, hazy reaction mixture was then heated and maintained under reflux conditions, while the mixture was slowly getting clear. While the reaction was progressing, the accumulating water was removed using a water separator. The reaction was terminated after 6 hours.

The clear solution resulting from above reaction was washed three times with a warm solution of $NaHCO_3$/NaCl (containing 4 parts 1N $NaHCO_3$ in water and 1 part saturated NaCl solution in water), and three times with a ethanol/NaCl solution (containing 4 parts aqueous ethanol (10% ethanol) and 1 part saturated NaCl solution in water). The phase separations took place slowly. The organic phase was then dried over sodium sulfate, and concentrated using a rotary evaporator. Remaining solvents were removed in a vacuum drying cabinet at 50° C.

358.6 g of product (yellow, viscous) were obtained, corresponding to 95.8% of the theoretical yield (374.3 g).

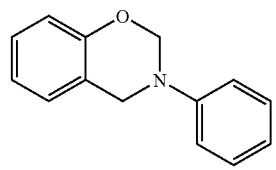

N-phenyl benzoxazine

Sample Preparation, Curing and Characterisation

In a 500 ml three-necked round bottom flask, 160 g of a benzoxazine resin and 40 g of a toughener were stirred under vacuum conditions (<1 mbar) at 105-110° C. for about 15 minutes, until the toughener was homogeneously dissolved in the benzoxazine resin. The resulting product was stored in a closed container at room temperature. The different compositions are shown in Table 1.

TABLE 1

| Composition (% (w/w)) | MDA-PB | A-B | B-Mix 6/4 | PU I | PU II | PU III | TBox I | TBox II | TBox III | TBox IV | TBox V |
|---|---|---|---|---|---|---|---|---|---|---|---|
| sample 1 | 100 | | | | | | | | | | |
| sample 2 | 80 | | | 20 | | | | | | | |
| sample 3 | 80 | | | | 20 | | | | | | |
| sample 4 | 80 | | | | | 20 | | | | | |
| sample 5 | 80 | | | | | | 20 | | | | |
| sample 6 | 80 | | | | | | | 20 | | | |
| sample 7 | 80 | | | | | | | | 20 | | |
| sample 8 | | 100 | | | | | | | | | |
| sample 9 | | 80 | | | | | | 20 | | | |
| sample 10 | | 80 | | | | | | | | 20 | |
| sample 11 | | 80 | | | | | | | | | 20 |
| sample 12 | | | 100 | | | | | | | | |
| sample 13 | | | 80 | | 20 | | | | | | |

Example 2

Production of a Mixture of a Benzoxazine Resin and a Toughener

As examples of benzoxazine resins, the following compounds were used:

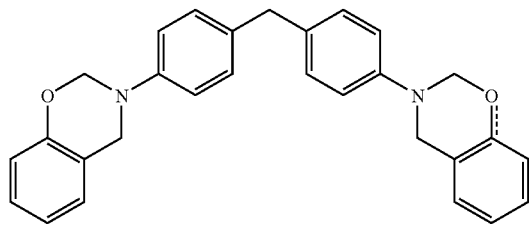

MDA-phenyl benzoxazine (MDA-PB)

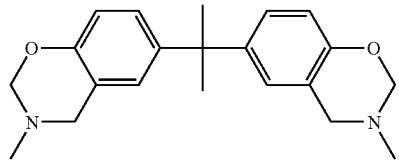

aliphatic benzoxazine (A-B)

and a mixture of 60% by weight of MDA-PB and 40% by weight of N-phenyl benzoxazine (B-Mix 6/4).

The products were cured in closed molds in a drying oven with air circulation at 180° C. for 3 hours. Then, the samples were taken out of the drying oven, released from the molds and cooled down at room temperature.

The cured samples were characterized using the following analytical methods:

The glass transition temperatures were obtained by dynamic-mechanical-thermal analysis (DMTA) of Samples cut to a size of 35 mm×10 mm×3.2 mm. The Samples were heated from 25° C. with a heating rate of 10° C./min to a final temperature of 250° C. The glass transition temperatures were obtained from the maximum value of the loss modulus vs. temperature diagrams. Flexural strength and flexural modulus were determined according to ASTM D790 using samples of a size of 90 mm×12.7 mm×3.2 mm, span=50.8 mm, speed=1.27 mm/min. K1c and G1c values were determined according to ASTM D5045-96 using so-called "single etch notch bending (SENS)" test specimens sized 56 mm×12.7 mm×3.2 mm.

Transmission Electron Microscopy (TEM)

The Samples were cut with an ultramicrotom (from Reichert-Jung, Vienna, Austria, Ultracut E) to ultrathin sections of a thickness of 50 to 100 nm, which were placed onto copper grids (obtainable from Agar Scientific, Stansted, GB, 400 square mesh) and contrasted with ruthenium tetroxide or osmium tetroxide. Every 30 seconds during a period of 10 minutes, an ultrathin section was removed from the contrasting process and each ultrathin section was placed into a transmission electron microscope (from Philips, Eindhoven, NL, CM12) and digital photographs were taken with a camera system (from Soft Imaging Systems GmbH, Biocam 0124/Analysis Pro 3,0). Each pixel of the TEM photograph was digitalized via the camera system, i.e. the brightness value is converted to a number. The exposure time is chosen in a way that each pixel is transmitted without information loss (total range of shades of grey and maximum brightness). The TEM photographs of the benzoxazine-based ultrathin sections show second domains (appearing dark) in a bright matrix.

From all TEM photographs of all ultrathin sections the TEM photograph was chosen for quantitative analysis that showed the maximum difference in brightness between the second domains and the bright matrix.

The second domains were analysed quantitatively with the software program "Analysis 5.0 Build 1080" from Soft Imaging System GmbH, Minster, Germany. The parameters for the analysis with said software program are chosen in a way that the second domains are visible on the TEM photographs.

The material properties of the cured samples are shown in Table 2.

2. The curable composition according to claim 1, wherein the at least one toughening additive is covalently bound to the at least one benzoxazine.

3. The curable composition according to claim 1, wherein the content of the thermoplastic toughening additive based on the total weight of the composition is 1 to 50% by weight.

4. The curable according claim 3, wherein the content of the thermoplastic toughening additive based on the total weight of the composition is 5 to 30% by weight.

5. The curable composition according to claim 1, further comprising a curable resin other than (a) and (b).

6. The curable composition cured product according to claim 1, further comprising one or more of extenders, microspheres, nanosilica particles, fillers, reinforcing agents, metal powders, pigments, dyes, fire-retarding agents, thixotropic agents, flow control agents, adhesion promoters, antioxidants and light stabilizers.

7. The curable composition according to claim 1, wherein the isocyanate-terminated prepolymer is represented by P—(X—CO—NH-D-NH—CO—Y-E)$_z$   formula (PP-I)

wherein P is a z-valent residue of an oligomer or polymer;
X and Y independently are selected from the group con-

TABLE 2

Material properties of the cured samples

| Property | 1 (ref.) | 2 | 3 | 4 | 5 | 6 | 7 | 8 (ref.) | 9 | 10 | 11 | 12 | 13 |
|---|---|---|---|---|---|---|---|---|---|---|---|---|---|
| DMTA-Tg (E') [° C.] | 200 | 193 | 199 | 192 | 193 | 193 | 197 | 187 | 191 | 185 | 192 | 156 | 141 |
| Flexural strength [MPa] | 170 | 130 | 135 | 70 | 115 | 126 | 110 | 106 | 115 | 96 | 119 | 151 | 131 |
| Flexural Modulus [MPa] | 4650 | 4000 | 3500 | 3400 | 3300 | 3150 | 2750 | 4400 | 3150 | 2900 | 2800 | 4950 | 3500 |
| K1c [MPa m$^{0.5}$] | 0.78 | 1.22 | 1.27 | 1.18 | 0.98 | 1.20 | 0.91 | 0.76 | 1.12 | 0.68 | 1.20 | 1.05 | 1.92 |
| G1c [J/m$^2$] | 115 | 230 | 404 | 359 | 252 | 396 | 264 | 114 | 350 | 138 | 453 | 197 | 924 |
| TEM morphology type | 1 | 2 | 2 | 2 | 2 | 2 | 3 | 1 | 2 | 2 | 2 | 1 | 2 |

TEM morphology type 1: No discrete domains
TEM morphology type 2: Matrix comprising discrete domains; at least 50% of the discrete domains related to the total amount of discrete domains have a maximum length in any direction of space in the range of 10 nm to 500 nm
TEM morphology type 3: Matrix comprising discrete domains; at least 50% of the discrete domains related to the total amount of discrete domains have a maximum length in one direction of space which is greater than 500 nm.

The invention claimed is:

1. A curable composition comprising:
   (a) at least one thermosetting benzoxazine resin and
   (b) at least one thermoplastic toughening additive soluble in the at least one thermosetting benzoxazine resin prior to curing and reactive with the at least one thermosetting benzoxazine resin in the curing process,
wherein the at least one thermoplastic toughening additive is a benzoxazine macromonomer or an isocyanate-terminated prepolymer,
   wherein prior to curing, the curable composition is homogeneous but when the curable composition is cured to form a cured product, phase separation is observed with the thermoplastic toughening additive distributed in the cured product in the form of discrete domains therein, and wherein at least 60% of the discrete domains have a maximum length in any direction of space in the range of 25 nm to 200 nm as determined by transmission electron microscopy (TEM).

sisting of NR', O and S, wherein R' is hydrogen or a residue selected from the group consisting of aliphatic, heteroaliphatic, araliphatic, heteroaraliphatic, aromatic and heteroaromatic residues; D is a divalent residue of a diisocyanate comprising two isocyanate groups having different reactivity, from which the two isocyanate groups with different reactivity have been removed to form two binding sites (valences); E is an end-capping residue, selected from the group consisting of aliphatic, heteroaliphatic, araliphatic, heteroaraliphatic, aromatic and heteroaromatic residues; and z is an integer of 1 to 12.

8. The curable composition according to claim 1, wherein the thermosetting benzoxazine resin comprises the combination of multifunctional benzoxazines and monofunctional benzoxazines.

9. The curable composition according to claim 1, wherein the benzoxazine macromonomer contains at least 3 benzoxazine rings and at least one aliphatic, heteroaliphatic, araliphatic, hetereoaraliphatic, aromatic or heteroaromatic fragment, the fragment comprising a shortest atom chain containing at least 40 consecutive atoms between two benzoxazine nitrogen atoms or between two benzoxazine oxygen atoms, and said atom chain must not include any oxazine ring atoms.

* * * * *